(12) United States Patent
Vaitaitis

(10) Patent No.: US 9,750,456 B2
(45) Date of Patent: Sep. 5, 2017

(54) METHOD AND SYSTEM OF ATTACHMENT AND DETECTION OF ATTACHMENT OF A WEARABLE SENSOR TO CLOTHING MATERIAL

(71) Applicant: MONDEVICES INC., North Bergen, NJ (US)

(72) Inventor: Arturas Henrikas Vaitaitis, North Bergen, NJ (US)

(73) Assignee: MONDEVICES INC., North Bergen, NJ (US)

( * ) Notice: Subject to any disclaimer, the term of this patent is extended or adjusted under 35 U.S.C. 154(b) by 184 days.

(21) Appl. No.: 14/578,904

(22) Filed: Dec. 22, 2014

(65) Prior Publication Data

US 2015/0190052 A1 Jul. 9, 2015

Related U.S. Application Data

(60) Provisional application No. 61/923,460, filed on Jan. 3, 2014.

(51) Int. Cl.
*A61B 5/00* (2006.01)
*G08B 21/04* (2006.01)

(52) U.S. Cl.
CPC .... *A61B 5/6804* (2013.01); *A61B 2560/0266* (2013.01); *A61B 2562/16* (2013.01); *G08B 21/0453* (2013.01); *Y10T 29/49826* (2015.01)

(58) Field of Classification Search
CPC ....... A61B 5/68; A61B 5/6801; A61B 5/6805; A61B 5/6806; A61B 5/6813; G08B 21/0446; G08B 21/0453
See application file for complete search history.

(56) References Cited

U.S. PATENT DOCUMENTS

| | | | |
|---|---|---|---|
| 3,979,802 A * | 9/1976 | Bongartz | A44B 17/0052 24/107 |
| 5,542,157 A | 8/1996 | Herman | |
| 5,610,877 A * | 3/1997 | Adams | G04B 37/1433 368/10 |
| 8,541,745 B2 | 9/2013 | Dickinson et al. | |
| 2007/0260421 A1 | 11/2007 | Berner, Jr. et al. | |
| 2009/0048070 A1* | 2/2009 | Vincent | A63B 24/0021 482/8 |

(Continued)

FOREIGN PATENT DOCUMENTS

CN 102018504 4/2011
WO WO2009/148595 12/2009

OTHER PUBLICATIONS

International Search Report and Written Opinion for International Application No. PCT/US2014/071837, mailed Apr. 13, 2015. (7 pages).

*Primary Examiner* — Van Trieu
(74) *Attorney, Agent, or Firm* — Tutunjian & Bitetto, P.C.

(57) ABSTRACT

A method and system of universal, secure attachment with attachment detection mechanism, of a wearable sensor-unit to any article of clothing worn around the body in order to measure vital signals of a person, such as motion, movements and activity levels. The method and system permits: reliable attachment to any article of clothing; an attachment in any position to clothing or fabric worn by a person; and detection for the wearable sensor attachment to an article of clothing to minimize false alarms.

11 Claims, 4 Drawing Sheets

(56) References Cited

U.S. PATENT DOCUMENTS

| | | | |
|---|---|---|---|
| 2009/0100570 A1* | 4/2009 | Tuan | A41D 27/085 2/122 |
| 2010/0077420 A1* | 3/2010 | Nielsen | H04H 60/33 725/9 |
| 2012/0190936 A1 | 7/2012 | Rao et al. | |
| 2012/0238923 A1 | 9/2012 | Yamashita et al. | |
| 2013/0109997 A1* | 5/2013 | Linke | G06F 19/3418 600/549 |
| 2013/0119255 A1 | 5/2013 | Dickinson et al. | |
| 2014/0187900 A1* | 7/2014 | Pernu | A41F 1/00 600/390 |
| 2014/0296651 A1* | 10/2014 | Stone | A61B 5/6804 600/301 |

\* cited by examiner

METHOD AND SYSTEM OF ATTACHMENT AND DETECTION OF ATTACHMENT OF A WEARABLE SENSOR TO CLOTHING MATERIAL

CROSS REFERENCE TO RELATED APPLICATIONS

This application claims priority from U.S. Provisional Application Ser. No. 61/923,460 filed Jan. 3, 2014, the entire contents of which are incorporated herein by reference.

BACKGROUND

Technical Field

The present principles relate to wearable sensors. More particularly, it relates to a method of universal attachment of a wearable sensor to articles of clothing worn around the subject's body in order to measure body movement, motion and activity level by such a sensor or plurality of sensors. The invention also relates to a method of detecting the attachment of wearable sensor to clothing.

Related Art

Previous known approaches in the area of medical portable devices addressed the problem of measuring health status of adults through the use of restrictive and intrusive attachments of devices, fixed to body via tight straps and adhesive materials that are not applicable for infant and newborn care, as they restrict blood flow and irritate the fragile skin of subjects. Existing approaches presume that the signal coming of the sensor is reliable and do not deal with a method of improving the signal strength by finding the best position of the sensor.

An invention described in this art introduces a novel design for universal attachment of a non-restrictive wearable sensor to any article of clothing in a position best suited for measurement of vital health signals, such as but not limited to body movements, sound, light, pressure, proximity, conductance, activity levels, heart rate, blood oxygen level and temperature. The sensor unit is worn on clothing without restricting the blood flow through the extremities of the subject.

Existing approaches require a specific static placement of wearable sensors, such as into pockets or on wristbands, or special clothing with embedded sensors. Existing approaches also do not ensure safeguards against incorrect placement. Incorrect placement of the sensor will result in false alarms or aberrant measurements. Some embodiments of invention described here include a method for detection if the sensor is attached to the clothing in a secure manner and ready for operation or if it is detached, thus providing some safeguards against incorrect attachment and minimizing amount of false alarms.

Methods and devices for clothing detection about a wearable electronic device—U.S. Pat. No. 8,541,745 B2. This publication is materially and significantly different from the art described in this invention, as it deals with the devices worn in pockets and around wristbands and do not address universal placement of a sensor anywhere on article of clothing, nor with detection of such attachment.

Wearable electronic system—WO2009148595 A2. This art is sufficiently different from the art of this invention, as it focuses on plurality of wearable components into a single assembly.

Wearable system for monitoring parameters of four vital signs of human bodies in real time—CN102018504 B.

This art is sufficiently different from this invention, as it describes placement of sensors on a wristwatch, a belt and on specific places on clothing.

SUMMARY

According to an implementation, the method for attaching and securing a wearable sensor to an article of clothing includes providing a sensor clip-on casing having a surface defining an opening and providing a sensor configured to be received into the opening of the clip-on casing. An article of clothing is position between the opening of the sensor clip-on casing and the sensor, and the sensor is squeezed or pushed into the opening of the sensor clip-on casing such that the article of clothing is sandwiched between the sensor and the sensor clip-on casing.

According to another implementation, the wearable sensor includes an outer clip-on casing having an opening, and a sensor assembly configured to be received and secured into the outer clip-on casing opening. When an article of clothing is positioned between the outer clip-on casing and the sensor before they are press fit together such that the same results in a secure fit between clip-on casing and sensor.

These and other aspects, features and advantages of the present principles will become apparent from the following detailed description of exemplary embodiments, which is to be read in connection with the accompanying drawings.

BRIEF DESCRIPTION OF THE DRAWINGS

The present principles may be better understood in accordance with the following exemplary figures, in which.

DETAILED DESCRIPTION

Figure 1:
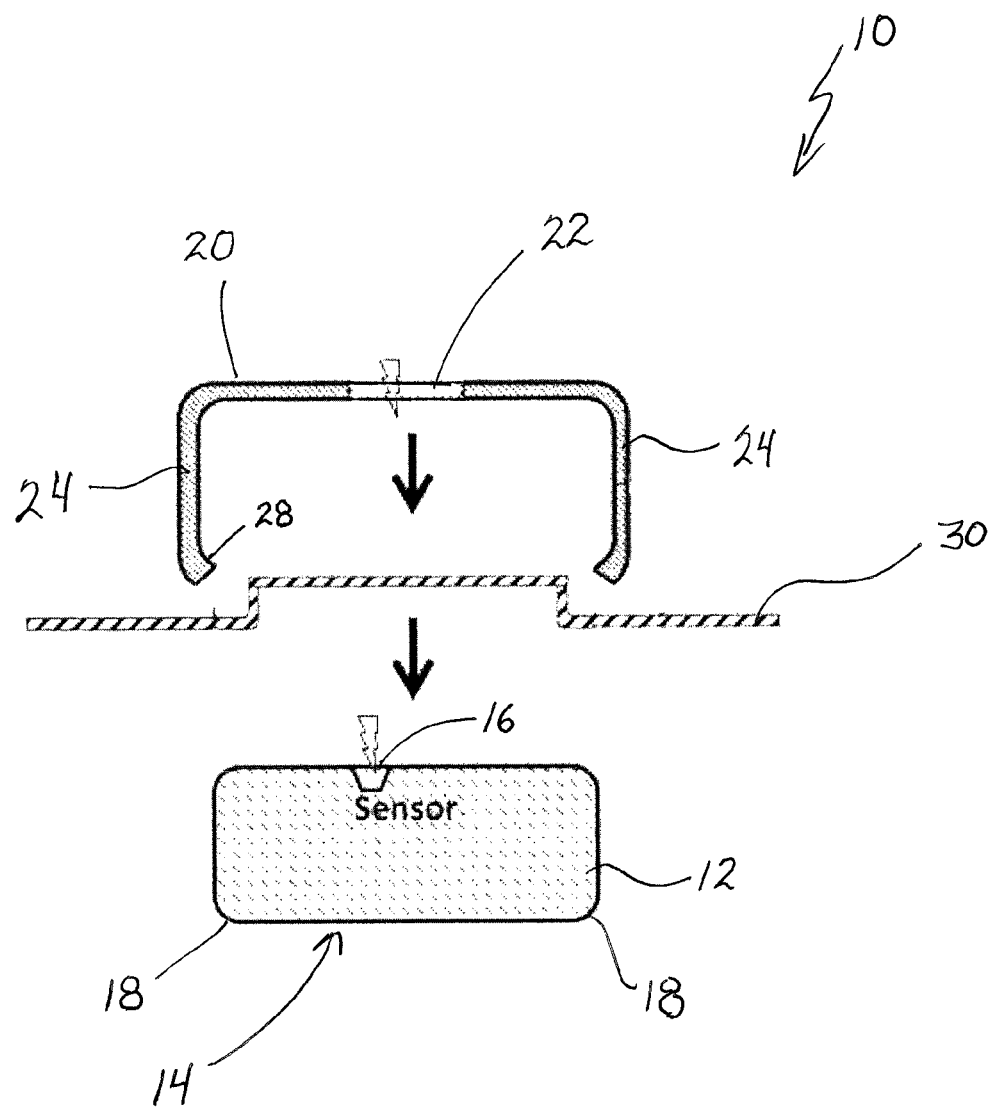
FIG. 1 is an exploded cross-sectional view of the wearable sensor not attached to an article of clothing, according to an embodiment of the invention.

The present principles are directed to wearable sensors and the attachment of the same to clothing of a wearer.

The present description illustrates the present principles. It will thus be appreciated that those skilled in the art will be able to devise various arrangements that, although not explicitly described or shown herein, embody the present principles and are included within its spirit and scope.

All examples and conditional language recited herein are intended for pedagogical purposes to aid the reader in understanding the present principles and the concepts contributed by the inventor(s) to furthering the art, and are to be construed as being without limitation to such specifically recited examples and conditions.

Moreover, all statements herein reciting principles, aspects, and embodiments of the present principles, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein represent conceptual views of illustrative circuitry embodying the present principles. Similarly, it will be appreciated that any flow charts, flow diagrams, state transition diagrams, pseudocode, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read-only memory ("ROM") for storing software, random access memory ("RAM"), and non-volatile storage.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

In the claims hereof, any element expressed as a means for performing a specified function is intended to encompass any way of performing that function including, for example, a) a combination of circuit elements that performs that function or b) software in any form, including, therefore, firmware, microcode or the like, combined with appropriate circuitry for executing that software to perform the function. The present principles as defined by such claims reside in the fact that the functionalities provided by the various recited means are combined and brought together in the manner which the claims call for. It is thus regarded that any means that can provide those functionalities are equivalent to those shown herein.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

FIG. 1 depicts a wearable sensor-unit 10 before attachment to an article of clothing. This figure demonstrates a method of universal attachment. As shown, the sensor 10 includes a sensor part 12 and an clip-on casing 20. The sensor 12 includes a bottom or lower surface 14, contoured lower corners 18, and an optical sensor 16. The clip-on casing 20 includes a window or opening 22 in a top surface thereof and side surface 24. The bottom of surface 24 has slightly curved in portions 28 configured to frictionally grip onto the lower corners 18 of the sensor 12. Examples of materials that can be used for the clip-on casing 20 and/or the sensor part 12 are any materials that have been considered safe for children, such as, for example, ABS plastic (i.e., Acrylonitrile Butadiene Styrene). Those of skill in the art will appreciate that other materials could be used for the clip-on casing 20 and/or the sensor 12 without departing from the intended scope of the present disclosure.

The sensor 12 includes an optical sensor 16 in an upper surface thereof and a corresponding window or opening 22 in the clip-on casing 20. Thus, when the sensor 12 is either not fastened to the clip-on casing 20, or is fastened therein without being attached to an article of clothing, light will pass unimpeded to optical sensor 16, thus indicating that the same is not attached to an article of clothing. As will be discussed further below, sensor 12 will transmit a signal to a remote device (e.g., computing device such as a smartphone, or other computing device) thus indicating that the same is not attached to an article of clothing. Further details on the internal workings of sensor 12 are discussed below with reference to FIG. 4.

Figure 2:
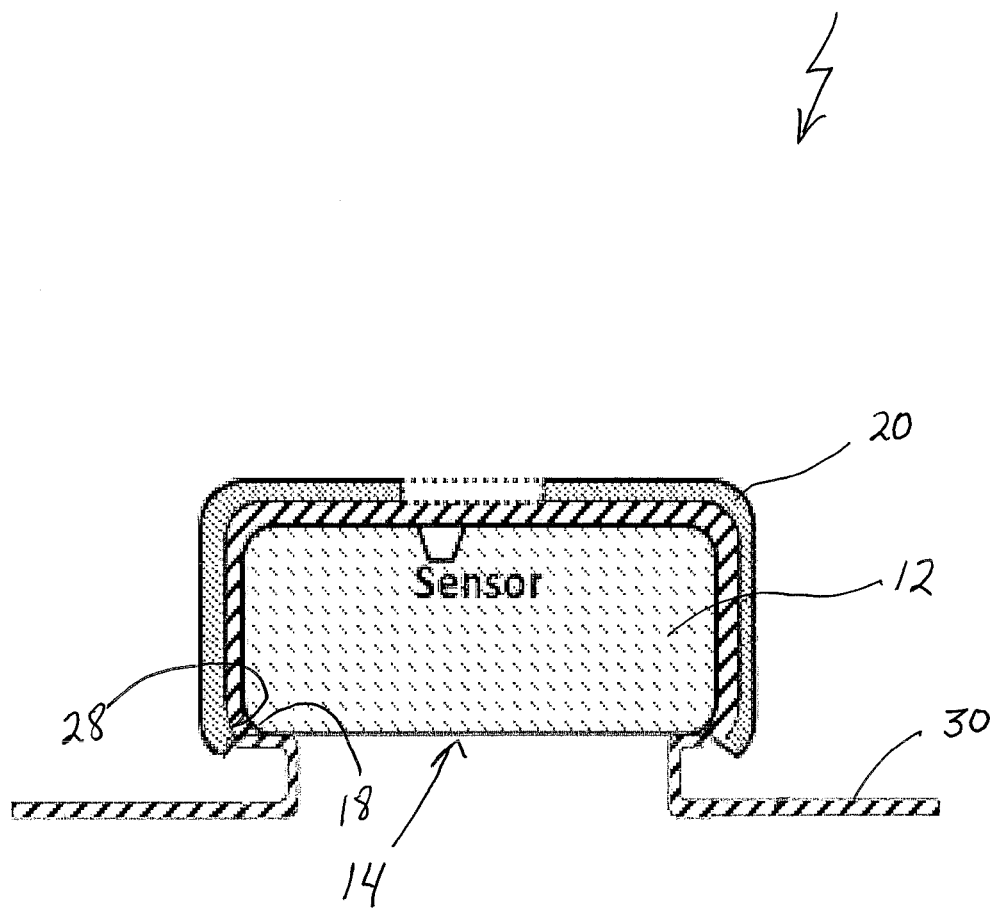
FIG. 2 is a cross-sectional view of the wearable sensor attached to an article of clothing, according to an embodiment of the invention.

FIG. 2 shows the wearable sensor 10 attached to an article of clothing 30. To achieve that state, a user-operator has to place clothing material 30 in between the external clip-on casing 20 and an internal housing containing sensor 12. Then a user-operator presses the internal housing containing sensor 12 into the external clip-on casing 20 until the surface 24 snap over the lower corners they will securely fasten, confining clothing material in between. Thickness of clothing material will diminish margins within the attachment and add to the strength of attachment by making it more securely held. As shown, when the clothing 30 is sandwiched between the sensor 12 and clip-on casing 20, curved portions 28 frictionally engage the lower corners 18 and "snap" the sensor onto the clothing in a secure manner. The thickness of the clothing 30 increases the friction between the clip-on casing 20 and sensor 12, thus providing for a very secure attachment.

Once the sensor 12 is inserted into the clip-on casing 20, the clothing 30 will operate to block light from passing to optical sensor 16. In this manner, the sensor 12 will transmit a signal to the remote device (e.g., computing device such as a smartphone, or other computing device), thus indicating that the sensor has been attached to an article of clothing.

Figure 3:
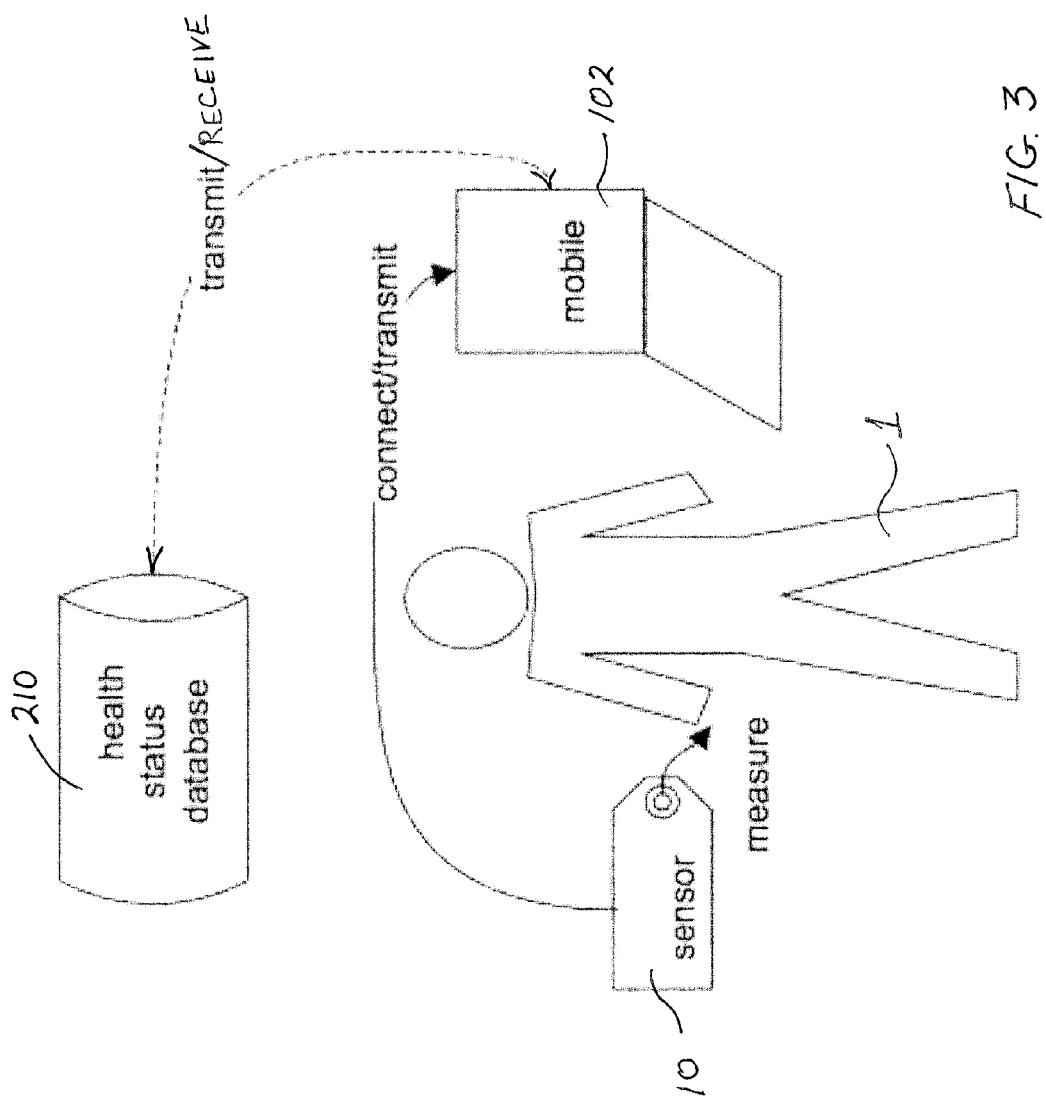
FIG. 3 is a schematic depiction of sensor-unit device, a subject of health monitoring, of a mobile reader device and their interactions according to an embodiment of the invention.

FIG. 3 shows a schematic diagram of the operation of wearable sensor 10. The user 1 attaches the sensor 10 to an article of their clothing (not shown). The sensor 10 is in remote communication with a mobile computing/reading device 102, such as, for example, a smartphone, a tablet, a laptop or any other suitable computing device. For home applications, the computing device need not be mobile, but it is preferred that computing device 102 is a mobile device.

The mobile reader device 102 is configured to measure, for example, a health status signal provide by the sensor. This health status signal can then be transmitted to a health status database 210. The health status database 210 can operate in many ways in accordance with the present principles. For example, health status database 210 can respond to the health status signal by sending a signal back to the mobile computing/reader device. This response can be an "all is ok" signal indicating that the health status of the individual has not changed in a manner that warrants any concern (e.g., signal received indicates that the monitored conditions are still within predetermined ranges for the same). Alternatively, the response could be "heart rate is high", "blood pressure" is low, or any other health related type of warning indicating that the monitored condition is now outside the predetermined ranges for that individual. In this case, an alert or trigger would be sent to the mobile reader 102. In this situation, a mobile reader device detects a transmitted alert, triggering an alarm within a mobile reader device environment. Alarm in a mobile reader device may be audible, visual or a combination of both, and may also include an audible and/or visual alert notification to a third party, such as hospital. In other alternatives, the mobile reader could send a text message or call a third party with a prerecorded message.

Figure 4:
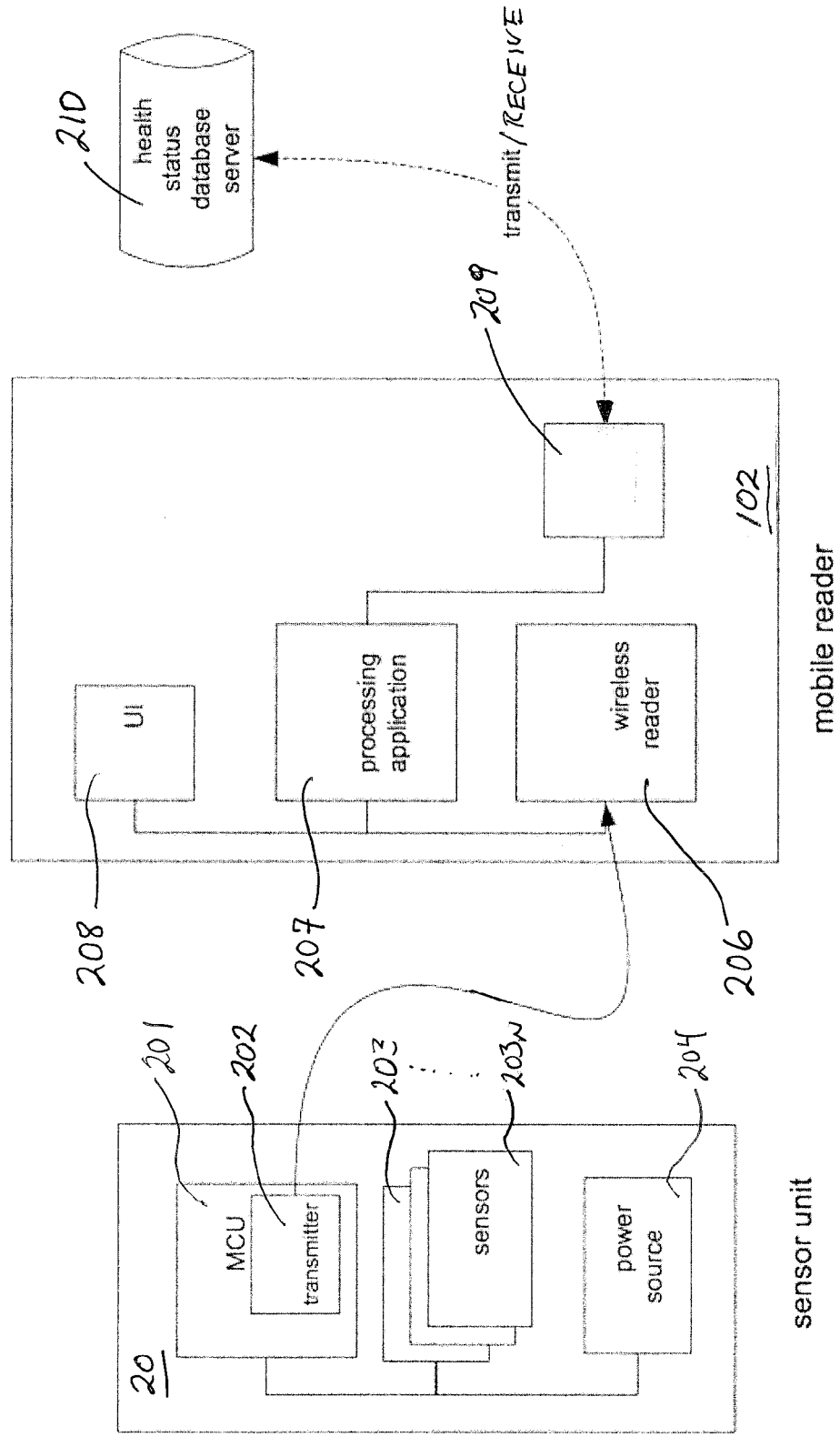
FIG. 4 is a block diagram of another implementation of the wearable sensor with mobile reader and an external health monitoring system, according to an embodiment of the invention.

As illustrated in FIG. 4, the sensor unit 20 consists of a micro-controller or processor 201, a low energy wireless transmitter 202, at least one sensor or array of sensors 203 and a power source 204 that powers the device and all sensor unit components. The mobile reader/computing device 102 consists of several components specific for a mobile device, however, only those of relevance to the present invention are disclosed. By way of example, the mobile device 201 includes a low energy reader 206, a processing application 207 running within a processor and to be displayed on a user interface 208 as a front end to show health status signal and alerts, and a wireless transmitter/receiver 209. As shown in the present example, mobile device 102 detects and reads sensor unit 20 by receiving wireless low energy signals transmitted from the sensor. The mobile device 102 may re-transmit the signal further via the wireless transmitter 209 to a third-party, such as the health status database server located off-site 210. Those of skill in the art will appreciate that the wireless transmitter/receiver 209 of the mobile device can be WiFi based, or RF based depending on the transmitting/receiving necessary.

According to one implementation, the sensor unit MCU 201 will store and run some software that uses the signal measured by an optical sensor 16 in order to detect if a wearable sensor is attached to clothing material. In this regard, those of skill in the art will appreciate that MCU 201 will either include its own memory, or the sensor unit 20 will have a memory component operating in conjunction with the MCU 201.

With respect to the one or more specific sensors 203 contained in the sensor device 20, a non-limiting list of examples of such sensors could be, for example, blood pressure, heart rate, temperature, sound, light, pressure, conductance etc. According to other contemplated embodiments, one sensor can measure and transmit a signal that is processed by the mobile device or health database to derive multiple sensed conditions from the received signal. By way of further example, through the use of accelerometers, the transmitted signal can include multiple readings which when deciphered/decoded by the mobile device or connected health database, things like position, movement (or lack thereof), activity levels, fall detection, tremors, etc. can all be derived and detected from the transmitted signal.

These and other features and advantages of the present principles may be readily ascertained by one of ordinary skill in the pertinent art based on the teachings herein. It is to be understood that the teachings of the present principles may be implemented in various forms of hardware, software, firmware, special purpose processors, or combinations thereof.

Most preferably, the teachings of the present principles are implemented as a combination of hardware and software. Moreover, the software may be implemented as an application program tangibly embodied on a program storage unit. The application program may be uploaded to, and executed by, a machine comprising any suitable architecture. Preferably, the machine is implemented on a computer platform having hardware such as one or more central processing units ("CPU"), a random access memory ("RAM"), and input/output ("I/O") interfaces. The computer platform may also include an operating system and microinstruction code. The various processes and functions described herein may be either part of the microinstruction code or part of the application program, or any combination thereof, which may be executed by a CPU. In addition, various other peripheral units may be connected to the computer platform such as an additional data storage unit and a printing unit.

It is to be further understood that, because some of the constituent system components and methods depicted in the accompanying drawings are preferably implemented in software, the actual connections between the system components or the process function blocks may differ depending upon the manner in which the present principles are programmed. Given the teachings herein, one of ordinary skill in the pertinent art will be able to contemplate these and similar implementations or configurations of the present principles.

Although the illustrative embodiments have been described herein with reference to the accompanying drawings, it is to be understood that the present principles is not limited to those precise embodiments, and that various changes and modifications may be effected therein by one of ordinary skill in the pertinent art without departing from the scope or spirit of the present principles. All such changes and modifications are intended to be included within the scope of the present principles as set forth in the appended claims.

What is claimed is:

1. A method for attaching and securing a wearable sensor to an article of clothing, the method comprising:
   providing a sensor clip-on casing having a surface defining an opening;
   providing a sensor configured to be received into the opening of the clip-on casing;
   positioning an article of clothing between the opening of the sensor clip-on casing and the sensor;
   squeezing the sensor into the opening sensor clip-on casing such that the article of clothing is sandwiched between the sensor and the sensor clip-on casing, said wearable sensor being positioned adjacent a skin of a user, and being further configured to be in intermittent direct contact with the skin of the user when the article of clothing is worn.

2. The method according to claim 1, further comprising detecting whether the wearable sensor is attached to an article of clothing.

3. The method according to claim 2, wherein said detecting comprises:
   determining if light is being received by an optical sensor contained on an upper surface of the sensor;
   when light is being received by the optical sensor, transmitting a signal to a remote device indicating that the wearable sensor is not attached to an article of clothing; and
   when light is not being received by the optical sensor, transmitting a signal to a remote device indicating that the wearable sensor is attached to an article of clothing.

4. The method according to claim 1, further comprising providing a remote computing device configured to read signals transmitted by the sensor.

5. The method according to claim 4, further comprising providing an off-site health database in communication with the remote computing device, said off side health database being configured to:
   receive sensor signals from the remote computing device;

compare the received signals to predetermined ranges of data relating to the user and the sensed condition relating to the received signal; and transmit response signals to the remote computing device based on such comparison.

6. A wearable sensor comprising:

an outer clip-on casing having an opening; and a sensor assembly configured to be received and secured into the outer clip-on casing opening;

wherein an article of clothing is positioned between the outer clip-on casing and the sensor such that the same results in a secure fit between clip-on casing and sensor, said sensor being positioned adjacent a skin of a user, and being further configured to be in intermittent direct contact with the skin of the user when the article of clothing is worn.

7. The wearable sensor according to claim 6, wherein said sensor assembly further comprises:

a micro-controller;

a transmitter in signal communication with the micro-controller;

at least one sensor in signal communication with the micro-controller; and a power source connected to the micro-controller, transmitter and the at least one condition specific sensor.

8. The wearable sensor according to claim 7, wherein the at least one sensor comprises one or more accelerometers.

9. The wearable sensor according to claim 7, wherein the at least one sensor comprises at least one of a blood pressure sensor, a light sensor, a sound sensor, a pressure sensor, a proximity sensor, a conductance sensor, a heart rate sensor and a temperature sensor.

10. The wearable sensor according to claim 7, further comprising a mobile computing device in signal communication with the sensor, the mobile computing device configured to receive transmitted signals from the wearable sensor.

11. The wearable sensor according to claim 10, further comprising a remotely located health status database in signal communication with the mobile device, said health status database being configured to analyze transmitted signals received from the mobile device relating to sensor measurements and provide status indications back to the mobile device relating to the same.

* * * * *